United States Patent
Cai et al.

(10) Patent No.: US 12,046,005 B2
(45) Date of Patent: Jul. 23, 2024

(54) TRANSCRANIAL MAGNETIC STIMULATION DIAGNOSTIC AND TREATMENT DEVICE

(71) Applicant: WUHAN ZNION TECHNOLOGY CO., LTD, Hubei (CN)

(72) Inventors: Shengan Cai, Hubei (CN); Cong Sun, Hubei (CN); Bo Wang, Hubei (CN)

(73) Assignee: WUHAN ZNION TECHNOLOGY CO., LTD (CN)

( * ) Notice: Subject to any disclaimer, the term of this patent is extended or adjusted under 35 U.S.C. 154(b) by 751 days.

(21) Appl. No.: 17/279,219

(22) PCT Filed: Feb. 26, 2019

(86) PCT No.: PCT/CN2019/076105
§ 371 (c)(1),
(2) Date: Mar. 24, 2021

(87) PCT Pub. No.: WO2020/062774
PCT Pub. Date: Apr. 2, 2020

(65) Prior Publication Data
US 2022/0031408 A1 Feb. 3, 2022

(30) Foreign Application Priority Data

Sep. 27, 2018 (CN) .......................... 201811131181.6

(51) Int. Cl.
*G06T 7/73* (2017.01)
*A61B 34/10* (2016.01)
(Continued)

(52) U.S. Cl.
CPC ................ *G06T 7/75* (2017.01); *A61B 34/10* (2016.02); *A61B 34/30* (2016.02); *A61N 2/006* (2013.01);
(Continued)

(58) Field of Classification Search
CPC ............. G06T 7/75; G06T 2207/10024; G06T 2207/10028; G06T 2207/30004;
(Continued)

(56) References Cited

U.S. PATENT DOCUMENTS

2009/0227830 A1* 9/2009 Pillutla .................... A61N 2/02
600/13
2013/0085316 A1* 4/2013 Fox ......................... A61N 2/02
600/13
(Continued)

FOREIGN PATENT DOCUMENTS

CN 201010235826.8 12/2010

*Primary Examiner* — Sunita Reddy

(57) ABSTRACT

A transcranial magnetic stimulation diagnostic and treatment device includes a horizontal translation platform, a base, an articulated robot, a TMS coil, a 3D camera, and a computer, where the base is provided with a controller, and the controller is respectively electrically connected to the horizontal translation platform, the articulated robot, the 3D camera, and the computer; the articulated robot and the horizontal translation platform are both provided above the base; a clamping part of the articulated robot clamps the TMS coil. The data of the head of a patient is acquired by the 3D camera, modeling is performed by the computer on the head of the patient, a position of a stimulation target on the head of the patient is determined, and the TMS coil is moved by the articulated robot to the stimulation target on the head of the patient to carry out magnetic stimulation treatment.

10 Claims, 7 Drawing Sheets

(51) Int. Cl.
*A61B 34/20* (2016.01)
*A61B 34/30* (2016.01)
*A61N 2/00* (2006.01)
*A61N 2/02* (2006.01)
*G06V 40/16* (2022.01)
*H04N 13/296* (2018.01)

(52) U.S. Cl.
CPC ............. *A61N 2/02* (2013.01); *G06V 40/161* (2022.01); *H04N 13/296* (2018.05); *A61B 2034/105* (2016.02); *A61B 2034/2057* (2016.02); *G06T 2207/10024* (2013.01); *G06T 2207/10028* (2013.01); *G06T 2207/30004* (2013.01); *G06T 2207/30201* (2013.01)

(58) Field of Classification Search
CPC .......... G06T 2207/30201; A61B 34/10; A61B 34/30; A61B 2034/105; A61B 2034/2057; A61N 2/006; A61N 2/02; G06V 40/161; H04N 13/296

USPC ...................................................... 600/9–15
See application file for complete search history.

(56) References Cited

U.S. PATENT DOCUMENTS

| | | | |
|---|---|---|---|
| 2013/0345491 A1* | 12/2013 | Saitoh ................. | A61B 5/0042 382/131 |
| 2016/0001074 A1* | 1/2016 | Rohan ................ | A61N 1/36025 607/45 |
| 2017/0296838 A1* | 10/2017 | Asahina ............... | A61G 15/125 |
| 2017/0372006 A1* | 12/2017 | Mainkar ............... | G16H 20/40 |
| 2018/0250521 A1* | 9/2018 | Wölfel .................... | A61N 2/006 |
| 2019/0060659 A1* | 2/2019 | Ginhoux ................ | B32B 27/08 |
| 2019/0192874 A1* | 6/2019 | Shukla .................... | A61N 2/02 |

* cited by examiner

TRANSCRANIAL MAGNETIC STIMULATION DIAGNOSTIC AND TREATMENT DEVICE

FIELD

The present invention relates to the field of transcranial magnetic stimulation medical technologies, and in particular, to a transcranial magnetic stimulation diagnostic and treatment device.

BACKGROUND

According to statistics from the Mental Health Center of the Chinese Center for Disease Control and Prevention, the total number of patients with mental illness in China has exceeded 100 million at present, but the public's awareness of mental illness is less than 50%, and the consultation rate is even lower. At present, about 20% of the patients with mental illness receive timely treatment, and 80% of the patients with mental illness are not treated in time, or even receive the most basic treatment. The number of patients with severe mental illness is as high as 16 million. According to the latest statistical data from the IMS Health, the global consumption of drugs for mental illness have exceeded 36 billion U.S. dollars, accounting for 5% of the total drug sales. However, as far as China is concerned, the current mental illness drug market is still relatively small, accounting for about 1.5% of the total hospital sales. There are already more than 600 psychiatric hospitals in China, but compared with the increasing incidence of mental illness, there is still a great gap to the needs of patients with mental illness in quantity and quality. There are still a large number of patients with mental illness who cannot get professional, systematic, and effective treatment.

Transcranial Magnetic Stimulation (TMS) is a technique to generate an electric current in the local cerebral cortex by a pulsed magnetic field to temporarily activate or inhibit the cortex. In the current field of medical devices, the operation of a TMS treatment device is to control a TMS coil by manual operation or by fixing same using a support to treat a patient. Manual operation is very inconvenient, and the coil needs to be held by hand for a long time or needs to be fixed at a specific angle by a support. The patient does not have good experience, because the patient needs to sit and keep a posture and dare not move. Repositioning is required after the patient moves. Manual positioning is complicated and not accurate enough, so that a treatment effect of the patient is greatly reduced.

The Chinese patent with the application No. 201010235826.8 discloses a navigation-based TMS treatment system, which is composed of a small nuclear magnetic resonance imaging system, an optical positioning navigation system, and a transcranial magnetic stimulator, where the small nuclear magnetic resonance imaging system is connected to a microcomputer of the navigation-based TMS treatment system; the small nuclear magnetic resonance imaging system carries out scanning to obtain scanning imaging data and transmits same to a microcomputer database; the optical positioning navigation system in the navigation-based TMS treatment system invokes the imaging data to carry out three-dimensional model reconstruction; after the reconstruction, a stimulation coil is aligned, and guided to a fixing position, so that a stimulation focus of the coil coincides with a specified stimulation point. The present invention is convenient in operation, accurate in positioning, more targeted in stimulation, and powerful in function. However, this patent implements modeling the head of a patient by using a nuclear magnetic resonance imaging system. The nuclear magnetic resonance imaging system may cause some harm to health of the brain of the patient, and when optical positioning is performed on the head of the patient, the head of the patient needs to wear an optical positioning means, which reduces the experience of the patient. Moreover, the system requires the nuclear magnetic resonance imaging system, the optical positioning navigation system, and the transcranial magnetic stimulator and treatment costs are relatively high.

SUMMARY

The purpose of the present invention is to provide a transcranial magnetic stimulation diagnostic and treatment device for solving problems existing in the prior art. Data of the head of a patient is acquired by a 3D camera, modeling is performed by a computer on the head of the patient, a position of a stimulation target on the head of the patient is determined, and a TMS coil is moved by an articulated robot to the stimulation target on the head of the patient to carry out magnetic stimulation treatment. The labor intensity of doctors is reduced, and an influence caused by human errors on a treatment effect is also reduced. While a problem in the prior art of harm to health of the brain of a patient caused by using a nuclear magnetic resonance imaging system to model the head of the patient is solved, a problem of poor experience is brought to the patient because the patient needs to wear an optical positioning means when optical positioning is performed on the head of the patient.

In order to achieve the purposes above, the technical invention adopts the following technical solutions.

A transcranial magnetic stimulation diagnostic and treatment device, including a horizontal translation platform, a base, an articulated robot, a TMS coil, a 3D camera, and a computer, where the base is provided with a controller, and the controller is respectively electrically connected to the horizontal translation platform, the articulated robot, the 3D camera, and the computer; the articulated robot and the horizontal translation platform are both provided above the base; a clamping part of the articulated robot clamps the TMS coil.

One end of the horizontal translation platform is provided with a head rest, the head rest includes an upper rest cover, a bottom rest cover, and a rest installing support, the rest installing support is installed on the horizontal translation platform, the bottom rest cover is installed on the rest installing support, the upper rest cover is installed on the bottom rest cover, and both the upper rest cover and the bottom rest cover are of a concave structure, which can limit turning of the head of a patient without bringing any discomfort to the patient, or affecting magnetic stimulation treatment on the back of the head of the patient by the TMS coil.

Specifically, the articulated robot sequentially includes a robot base, a first mechanical arm, a second mechanical arm, a third mechanical arm, and a clamping part; a first rotary motor is provided at a part where the robot base is connected to the base, a second rotary motor is provided at a part where the first mechanical arm is connected to the robot base, a third rotary motor is provided at a part where the second mechanism arm is connected to the first mechanism arm, and a telescoping motor is provided at a part where the third mechanical arm is connected to the second mechanical arm.

Further, the robot base rotates, by means of the rotary motor, 360 degrees freely on a horizontal plane; the first mechanical arm rotates, by means of the second rotary motor, 180 degrees freely on a vertical plane about a connection part between the first mechanical arm and the robot base; the second mechanical arm rotates, by means of the third rotary motor, 180 degrees freely on the vertical plane about a connection part between the second mechanical arm and the first mechanical arm; the third mechanical arm performs, by means of the telescoping motor, telescopic movement back and forth on a straight line where the second mechanical arm and the third mechanical arm are located.

Specifically, a camera installing support is provided above the horizontal translation platform, the 3D camera is provided on the camera installing support, and the 3D camera is located right above the head rest and configured to acquire 3D image data of the head of the patient.

Further, a fourth rotary motor is provided at a part where the camera installing support is connected to the horizontal translation platform, and the camera installing support rotates, by means of the fourth rotary motor, in the vertical plane about the part where the camera installing support is connected to the horizontal translation platform, so that the 3D image data of the head of the patient is conveniently obtained.

Specifically, a heat dissipating window is formed on a side surface of the base and is configured to dissipate heat of the controller, so that the controller is prevented from being damaged due to excessive temperature.

Specifically, a plurality of gimbal locking wheels are provided on the bottom of the base, so as to conveniently move the treatment device.

Corresponding to the diagnostic and treatment device above, the present invention further provides a transcranial magnetic stimulation diagnostic and treatment method, including the following steps:

S1. making a patient lie on the horizontal translation platform, resting the head on the head rest, and controlling and adjusting, by the computer, a longitudinal position of the horizontal translation platform to position the head of the patient within an image acquisition range of the 3D camera;

S2. acquiring, by the 3D camera, 3D image data of the head of the patient and transferring the acquired 3D image data to the computer;

S3. processing, by the computer, the 3D image data to construct a head model of the patient;

S4. constructing, by the computer, a spatial coordinate system based on the 3D camera, and calculating, by using the 3D image data, three-dimensional coordinates of feature points of the head of the patient in the spatial coordinate system; matching the head model of the patient with the head of the patient in the spatial coordinate system, and determining three-dimensional coordinates of a stimulation target on the head of the patient in the spatial coordinate system; and S5. controlling, according to a spatial position of the stimulation target on the head of the patient, the articulated robot to move the TMS coil to the position of the stimulation target on the head of the patient to carry out magnetic stimulation treatment on the head of the patient.

Specifically, in step S5, the in the process of carrying out the magnetic stimulation treatment on the head of the patient, three-dimensional attitude information of the head of the patient is acquired by the 3D camera in real time, a latest spatial position of the stimulation target on the head of the patient is determined according to the three-dimensional attitude information acquired in real time, and finally, according to the latest spatial position of the stimulation target on the head of the patient, the articulated robot is controlled to move the TMS coil to the latest position of the stimulation target on the head of the patient to carry out precise magnetic stimulation treatment on the head of the patient in real time.

Compared with the prior art, the beneficial effects of the present invention are as follows: (1) in the present invention, a doctor does not need to hold a TMS coil or fix the TMS coil using a support to carry out magnetic stimulation treatment on the head of a patient; in the present invention, 3D image data of the head of the patient is acquired by a 3D camera, modeling is performed by a computer on the head of the patient, a precise position of a stimulation target on the head of the patient is determined, and a TMS coil is moved by an articulated robot to the vicinity of the stimulation target on the head of the patient to carry out magnetic stimulation treatment on the head of the patient; precision of the magnetic stimulation treatment is improved, the workload of doctors is reduced, and adverse effects caused by human factors on a treatment effect are avoided; (2) in a treatment process, a treatment device in the present invention acquires, by means of the 3D camera, three-dimensional attitude information of the head of the patient in real time, and determines a latest position of the stimulation target according to the real-time three-dimensional attitude information of the head of the patient, so that even if the attitude of the head of the patient changes in the treatment process, the precision of the magnetic stimulation treatment is still ensured, the patient does not need to keep a posture for a long term in the treatment process, and the user experience is improved; (3) in the present invention, the head rest has curved design, can limit large movement of the head of the patient without bringing any discomfort to the patient, or affecting magnetic stimulation treatment on the back of the head of the patient by the TMS coil.

Figure 1:
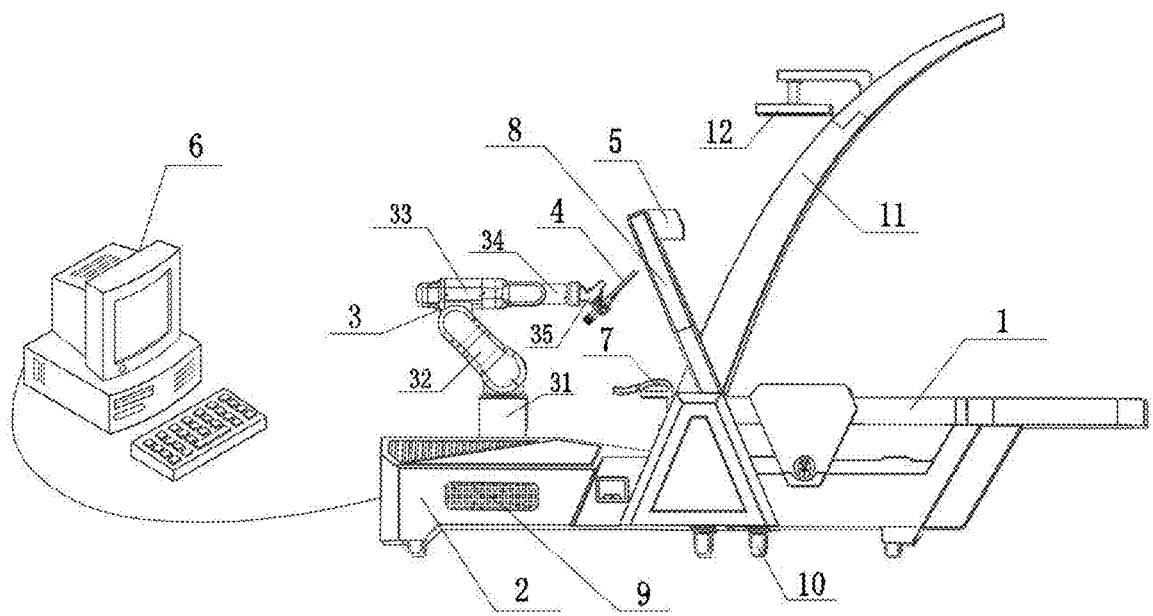
FIG. 1 is a schematic structural diagram of an entire transcranial magnetic stimulation diagnostic and treatment device according to embodiment 1.
Figure 2:
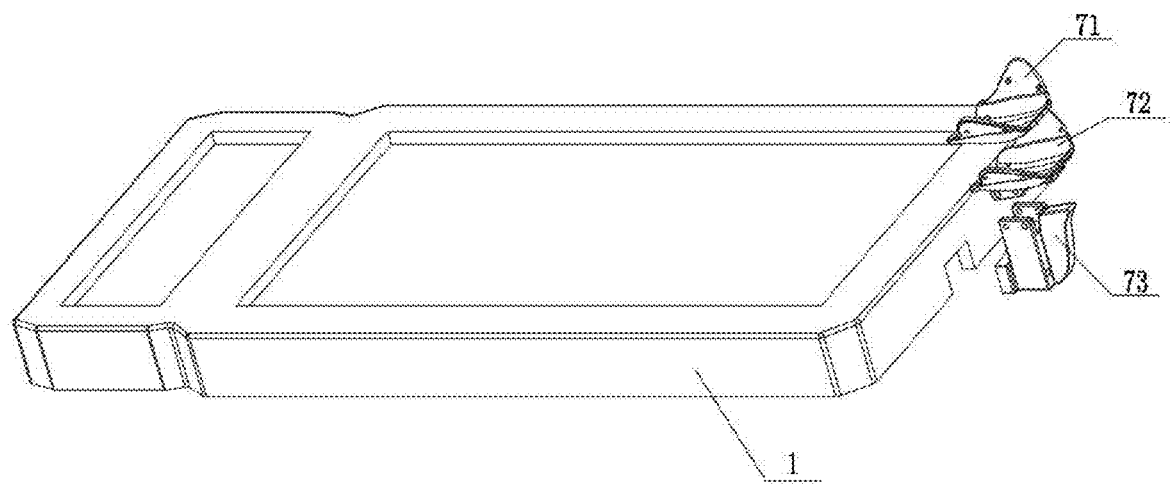
FIG. 2 is a schematic structural diagram of installation of a head rest and a horizontal translation platform in embodiment 1.
Figure 3A:
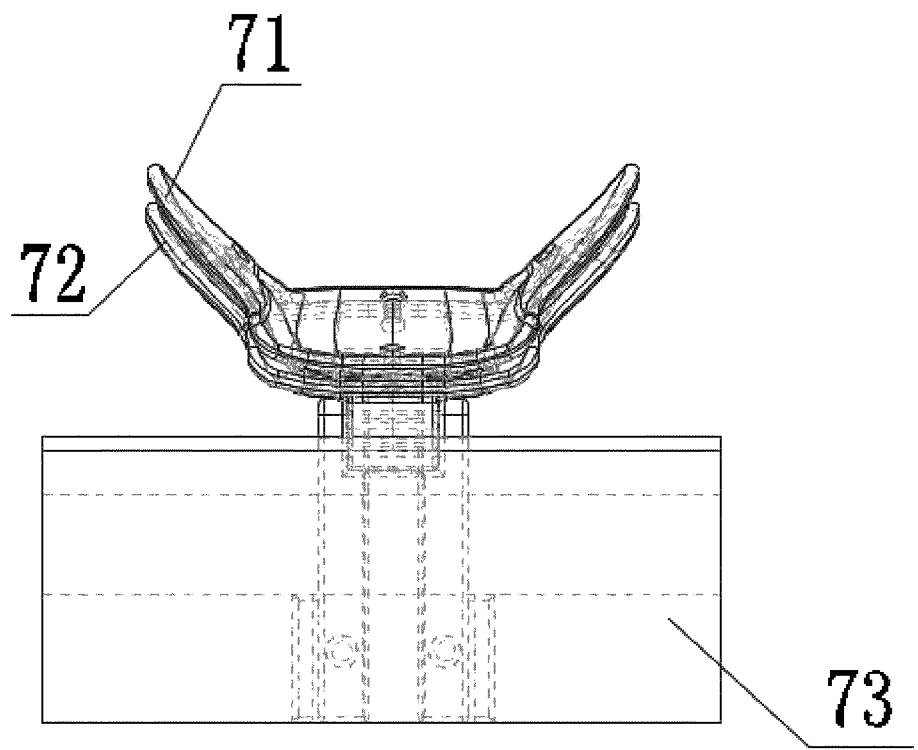
FIG. 3A is a front view of a head rest in embodiment 1.
Figure 3B:
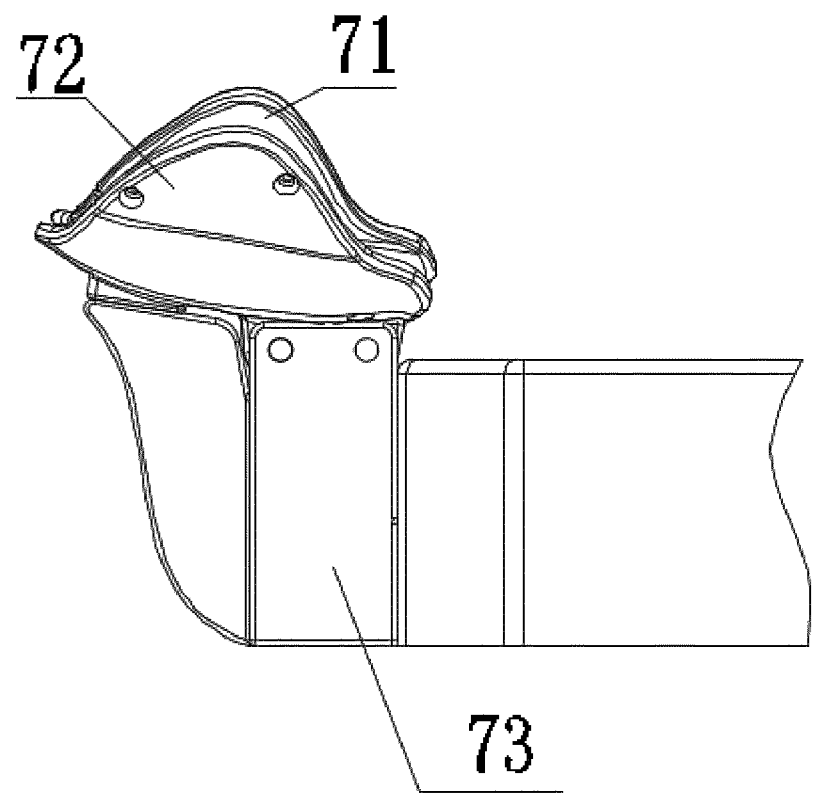
FIG. 3B is a left view of a head rest in embodiment 1.
Figure 3C:
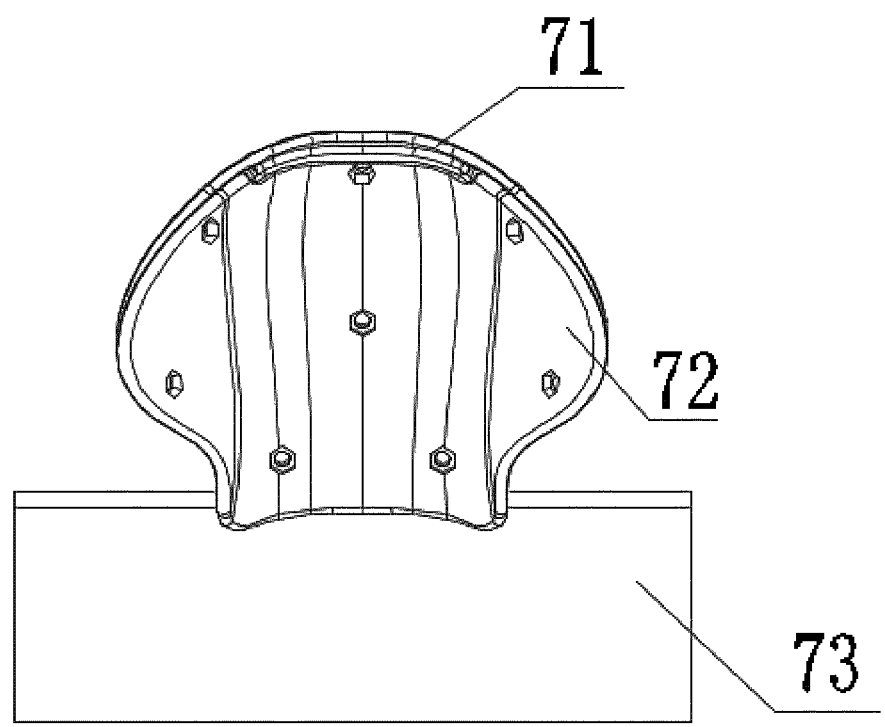
FIG. 3C is a top view of a head rest in embodiment 1.

in the drawings: 1. horizontal translation platform; 2. base; 3. articulated robot; 31. robot base; 32. first mechanical arm; 33. second mechanical arm; 34. third mechanical arm; 35. clamping part; 4. TMS coil; 5. 3D camera; 6. computer; 7. head rest; 71. upper rest cover; 72. bottom rest cover; 73. rest installing support; 8. camera installing support; 9. heat dissipating window; 10. gimbal locking wheel.

DETAILED DESCRIPTION

The technical solutions of the present invention are clearly and fully described below with reference to the accompanying drawings in the present invention. Apparently, the described embodiments are merely some of the embodiments of the present invention, but not all the embodiments. Based on the embodiments of the present invention, all other embodiments that may be implemented by persons of ordinary skill in the art without involving an inventive effort shall fall within the scope of protection of the present invention.

Embodiment 1

As shown in FIG. 1, the present embodiment provides a transcranial magnetic stimulation diagnostic and treatment device, including a horizontal translation platform 1, a base 2, an articulated robot 3, a TMS coil 4, a 3D camera 5, and a computer 6, where the base 2 is provided with a controller, and the controller is respectively electrically connected to the horizontal translation platform 1, the articulated robot 3, the 3D camera 5, and the computer 6; the articulated robot 3 and the horizontal translation platform 1 are both provided above the base 2; a clamping part 35 of the articulated robot 3 clamps the TMS coil 4.

As shown in FIG. 2 to FIG. 3A-3C, one end of the horizontal translation platform 1 is provided with a head rest 7, the head rest 7 includes an upper rest cover 71, a bottom rest cover 72, and a rest installing support 73, the rest installing support 73 is installed on the horizontal translation platform 1, the bottom rest cover 72 is installed on the rest installing support 73, the upper rest cover 71 is installed on the bottom rest cover 72, and both the upper rest cover 71 and the bottom rest cover 72 are of a concave structure. The head rest 7 mainly functions as a bracket, with support points being the skull and the neck, and limits turning of the head of a patient without bringing any discomfort to the patient, or affecting magnetic stimulation treatment on the back of the head of the patient by the TMS coil 4.

Specifically, four first installing holes are formed on the rest installing support 73, four second installing holes and six third installing holes are formed on the bottom rest cover 72, and six fourth installing holes are formed on the upper rest cover 71; the first installing holes correspond to the second installing holes for installing the bottom rest cover 72 on the rest installing support 73 by means of bolts; the third installing holes correspond to the fourth installing holes for installing the upper rest cover 71 on the bottom rest cover 72 by means of bolts; the rest installing support 73 is installed on the horizontal translation platform 1 by means of snap-fit.

Specifically, the articulated robot 3 sequentially includes a robot base 31, a first mechanical arm 32, a second mechanical arm 33, a third mechanical arm 34, and a clamping part 35; a first rotary motor is provided at a part where the robot base 31 is connected to the base 2, a second rotary motor is provided at a part where the first mechanical arm 32 is connected to the robot base 31, a third rotary motor is provided at a part where the second mechanism arm 33 is connected to the first mechanism arm 32, and a telescoping motor is provided at a part where the third mechanical arm 34 is connected to the second mechanical arm 33.

Further, the robot base 31 rotates, by means of the rotary motor, 360 degrees freely on a horizontal plane; the first mechanical arm 32 rotates, by means of the second rotary motor, 180 degrees freely on a vertical plane about a connection part between the first mechanical arm 32 and the robot base 31; the second mechanical arm 33 rotates, by means of the third rotary motor, 180 degrees freely on the vertical plane about a connection part between the second mechanical arm 33 and the first mechanical arm 32; the third mechanical arm 34 performs, by means of the telescoping motor, telescopic movement back and forth on a straight line where the second mechanical arm 33 and the third mechanical arm 34 are located.

Specifically, a camera installing support 8 is provided above the horizontal translation platform 1, the 3D camera 5 is provided on the camera installing support 8, and the 3D camera 5 is located right above the head rest 7 and configured to acquire 3D image data of the head of the patient.

Further, a fourth rotary motor is provided at a part where the camera installing support 8 is connected to the horizontal translation platform 1, and the camera installing support 8 rotates, by means of the fourth rotary motor, in the vertical plane about the part where the camera installing support 8 is connected to the horizontal translation platform 1, so that the 3D image data of the head of the patient is conveniently obtained.

Specifically, a heat dissipating window 9 is formed on a side surface of the base 2 and is configured to dissipate heat of the controller, so that the controller is prevented from being damaged due to excessive temperature.

Specifically, eight gimbal locking wheels 10 are provided on the bottom of the base 2, so as to conveniently move the treatment device.

Specifically, a display installing support 11 is further provided on the horizontal translation platform 1, and a display 12 is installed on the display installing support 11 for playing specified content to attract the patient to watch, so that the head is kept in a fixed attitude. The display 12 is fixed diagonally above the head of the patient, so as to improve the comfort level when the patient watches.

Embodiment 2

Figure 4:
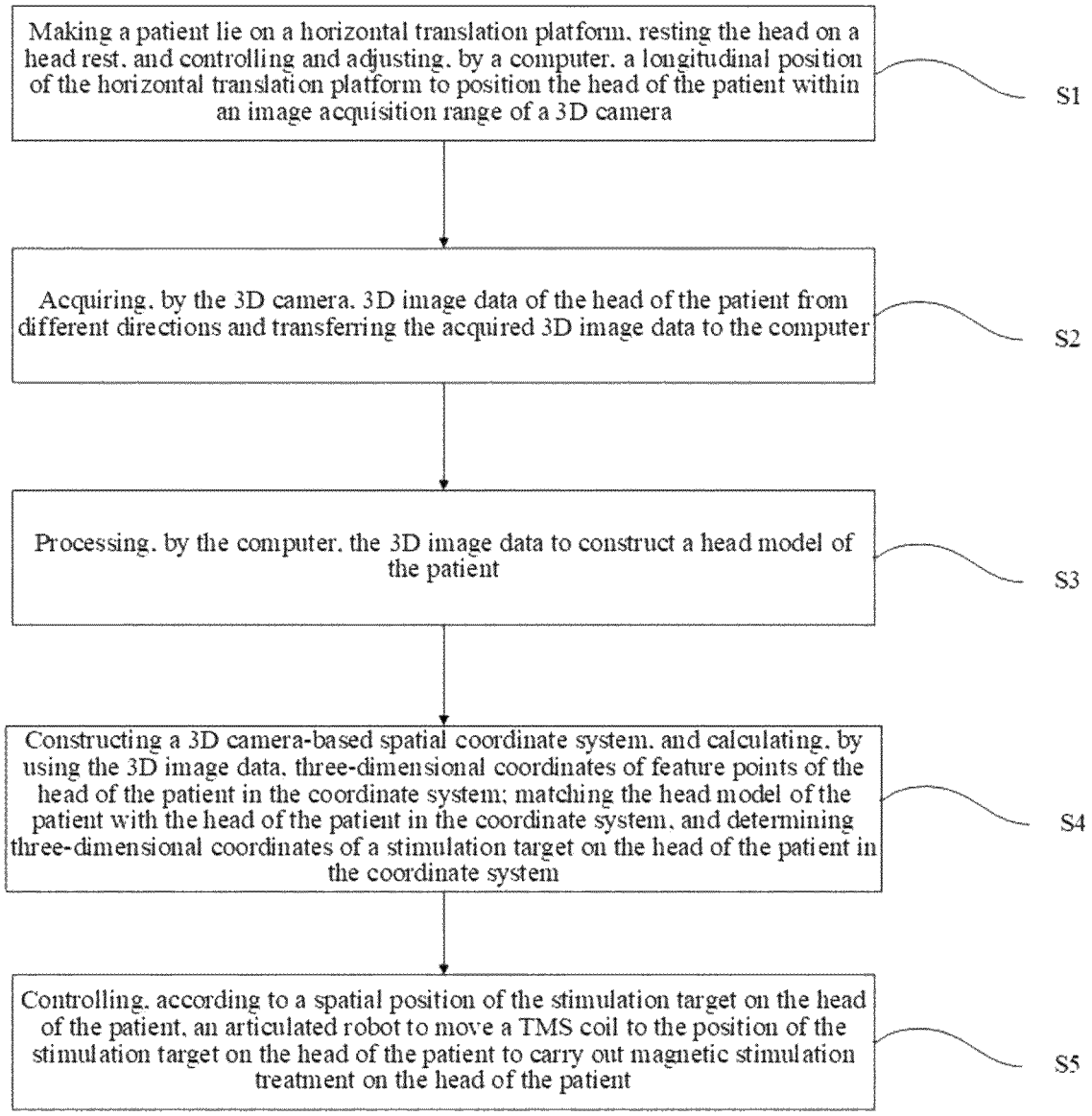
FIG. 4 is a schematic flowchart of a transcranial magnetic stimulation diagnostic and treatment method according to embodiment 2.
Figure 5:
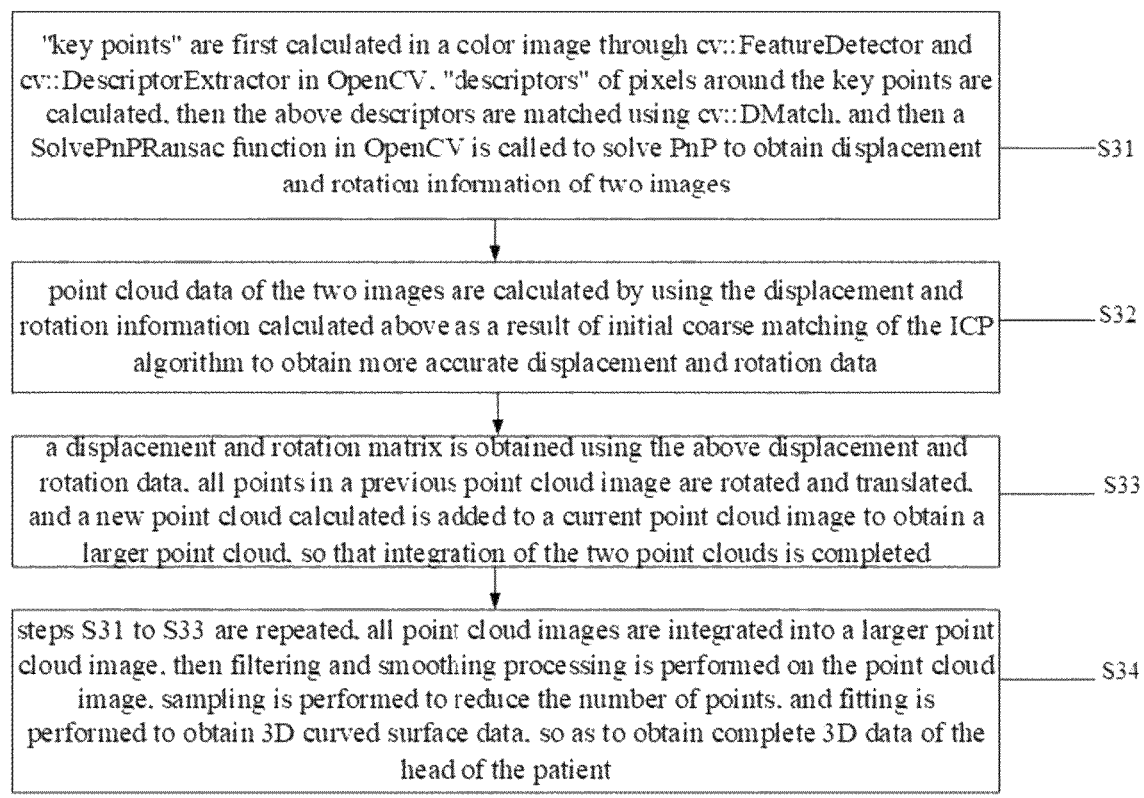
FIG. 5 is a schematic flowchart of the steps of stitching of point clouds.

As shown in FIG. 4, the present embodiment provides a transcranial magnetic stimulation diagnostic and treatment method, including the following steps.

S1. making a patient lie on the horizontal translation platform 1, resting the head on the head rest 7, and controlling and adjusting, by the computer 6, a longitudinal position of the horizontal translation platform 1 to position the head of the patient within an image acquisition range of the 3D camera 5;

S2. acquiring, by the 3D camera 5, 3D image data of the head of the patient and transferring the acquired 3D image data to the computer 6;

S3. processing, by the computer 6, the 3D image data to construct a head model of the patient;

S4. constructing, by the computer 6, a spatial coordinate system based on the 3D camera 5, and calculating, by using the 3D image data, three-dimensional coordinates of feature points of the head of the patient in the spatial coordinate system; matching the head model of the patient with the head of the patient in the spatial coordinate system, and determining three-dimensional coordinates of a stimulation target on the head of the patient in the spatial coordinate system; and S5. controlling, according to a spatial position of the stimulation target on the head of the patient, the articulated robot 3 to move the TMS coil 4 to the position of the stimulation target on the head of the patient to carry out magnetic stimulation treatment on the head of the patient.

Specifically, in step S5, follow-up positioning is further performed on the head of the patient by means of the 3D camera 5; in the treatment process, position information of the head of the patient each time positioning is completed is recorded, and if at a next moment, a distance between positions of a magnetic stimulation point at a current time and a previous time exceeds 5 mm due to movement of the head of the patient, follow-up positioning is started; if the distance does not exceed 5 mm, follow-up positioning is not started; if the head of the patient turns a lot of times, follow-up by the 3D camera 5 and the mechanical arm is suspended, and magnetic stimulation by the TMS coil 4 is also suspended; if the patient is not within an adjustable range of the 3D camera 5 or leaves, the mechanical arm and the magnetic stimulation action of the coil are stopped.

Specifically, follow-up positioning is specifically: determining a latest spatial position of the stimulation target on the head of the patient according to the position information acquired in real time, and finally, according to the latest spatial position of the stimulation target on the head of the patient, controlling the articulated robot 3 to move the TMS coil 4 to the latest position of the stimulation target on the head of the patient to carry out precise magnetic stimulation treatment on the head of the patient in real time.

Specifically, in step S3, the processing, by the computer 6, the 3D image data includes: calculating, by identifying feature points in images acquired in the various directions, a matching relationship between the images, then obtaining, through a 3D point cloud ICP algorithm, a spatial position relationship between point cloud images acquired in the various directions, and finally, performing rotation and translation operations on all point cloud image data according to the matching relationship and the spatial position relationship to obtain a complete 3D point cloud image of the head of the patient.

Further, modeling a head needs to acquire 3D scan data of the head of a patient by a 3D camera 5. Each time the 3D camera 5 performs photographing, a color image, a depth image, and a 3D point cloud image are generated. The three images are generated at the same time, and thus, points on the images have a fixed corresponding relationship. The corresponding relationship is known and is obtained through calibration of the camera. 3D scanning is to capture a series of images around the head of a patient, and then stitch the images into a complete image. Image stitching involves finding the same parts of two images and matching same. No 3D point cloud for hair can be obtained in a 3D camera 5, but 3D data of the skull (without hair) is needed in a medical treatment head model. Therefore, a patient needs to wear a specific positioning cap during scanning for a head model. In order to make the matching more accurate, some mark points are usually provided on the cap. 3D scanning ultimately needs to stitch 3D point clouds. The rotation and translation relationship between point clouds of all images is needed during stitching. The stitching of point clouds mainly relies on an ICP algorithm. The ICP algorithm sometimes fails, so rough matching is required first.

Further, stitching of point clouds includes the follow steps.

At S31, "key points" are first calculated in a color image through cv::FeatureDetector and cv::DescriptorExtractor in OpenCV, "descriptors" of pixels around the key points are calculated, then the above descriptors are matched using cv::DMatch, and then a SolvePnPRansac function in OpenCV is called to solve PnP to obtain displacement and rotation information of two images.

At S32, point cloud data of the two images are calculated by using the displacement and rotation information calculated above as a result of initial coarse matching of the ICP algorithm to obtain more accurate displacement and rotation data.

At S33, a displacement and rotation matrix is obtained using the above displacement and rotation data, all points in a previous point cloud image are rotated and translated, and a new point cloud calculated is added to a current point cloud image to obtain a larger point cloud, so that integration of the two point clouds is completed.

At S34, steps S31 to S33 are repeated, all point cloud images are integrated into a larger point cloud image, then filtering and smoothing processing is performed on the point cloud image, sampling is performed to reduce the number of points, and fitting is performed to obtain 3D curved surface data, so as to obtain complete 3D data of the head of the patient.

Finally, a head model of the head of the patient is constructed according to the complete 3D data of the head of the patient.

Specifically, in step S4, the head model of the patient is matched with the head of the patient in the spatial coordinate system, and the specific matching method includes: in the treatment process, a 3D image captured by the 3D camera 5 in real time only has facial information of the patient, no head information, so that the head model constructed in S3 needs to be aligned with facial data captured in real time in position; because the computation amount of the ICP algorithm is large, and requirements of real-time detection cannot be satisfied, a position alignment method involves first labeling facial features points (a position between the eyebrows, corners of the eyes, a tip of the nose, earlobes, corners of the mouth, etc.) for alignment in the head model, then automatically identifying the facial features points in a real-time image, calculating a conversion relationship between the real-time image and the head model by matching the feature points, calculating a position of the head model in the space, and then calculating position coordinates of a target on the head model in the space.

Although embodiments of the present invention are shown and described, it is obvious to those skilled in the art that it can be understood that various changes, modifications, substitutions and variations can be made on these embodiments without departing from the principles and spirit of the present invention. The scope of the present invention is limited by the attached claims and equivalent thereof.

What is claimed is:

1. A transcranial magnetic stimulation diagnostic and treatment device, comprising: a horizontal translation platform, a base, an articulated robot, a TMS coil, a 3D camera, and a computer, wherein,
   the base is provided with a controller, and the controller is respectively electrically connected to the horizontal translation platform, the articulated robot, the 3D camera, and the computer;
   the articulated robot and the horizontal translation platform are both provided above the base;
   a clamping part of the articulated robot clamps the TMS coil;
   the 3D camera is configured to acquire 3D image data of a head of a patient;
   the computer is configured to process the 3D image data to construct a three-dimensional model of the head of the patient and acquiring positions a position of the head of the patient and the TMS coil:
   the controller is configured to control the articulated robot to move the TMS coil to the position of the head of the patient;
   wherein,
   one end of the horizontal translation platform is provided with a head rest, the head rest comprises an upper rest cover, a bottom rest cover, and a rest installing support, the rest installing support is installed on the horizontal translation platform, the bottom rest cover is installed on the rest installing support, the upper rest cover is installed on the bottom rest cover, and both the upper rest cover and the bottom rest cover are of a concave structure.

2. The transcranial magnetic stimulation diagnostic and treatment device according to claim 1, wherein, the articulated robot comprises a robot base, a first mechanical arm, a second mechanical arm, a third mechanical arm, and a clamping part which are sequentially connected;

a first rotary motor is provided at a part where the robot base is connected to the base, a second rotary motor is provided at a part where the first mechanical arm is connected to the robot base, a third rotary motor is provided at a part where the second mechanism arm is connected to the first mechanism arm, and a telescoping motor is provided at a part where the third mechanical arm is connected to the second mechanical arm.

3. A diagnostic and treatment method based on the transcranial magnetic stimulation diagnostic and treatment device according to claim 2, comprising the following steps:

making the patient lie on the horizontal translation platform, resting a head of the patient on the head rest, and controlling and adjusting, by the computer, a longitudinal position of the horizontal translation platform to position the head of the patient within an image acquisition range of the 3D camera;

acquiring, by the 3D camera, 3D image data of the head of the patient and transferring the acquired 3D image data to the computer;

processing, by the computer, the 3D image data to construct a head model of the patient;

constructing, by the computer, a spatial coordinate system based on the 3D camera, and calculating, by using the 3D image data, three-dimensional coordinates of feature points of the head of the patient in the spatial coordinate system; matching the head model of the patient with the head of the patient in the spatial coordinate system, and determining three-dimensional coordinates of a stimulation target on the head of the patient in the spatial coordinate system; and controlling, according to a spatial position of the stimulation target on the head of the patient, the articulated robot to move the TMS coil to the position of the stimulation target on the head of the patient to carry out magnetic stimulation treatment on the head of the patient.

4. The transcranial magnetic stimulation diagnostic and treatment device according to claim 1, wherein, a camera installing support is provided above the horizontal translation platform, and the 3D camera is provided on the camera installing support.

5. A diagnostic and treatment method based on the transcranial magnetic stimulation diagnostic and treatment device according to claim 4, comprising the following steps:

making the patient lie on the horizontal translation platform, resting the head of the patient on the head rest, and controlling and adjusting, by the computer, a longitudinal position of the horizontal translation platform to position the head of the patient within an image acquisition range of the 3D camera;

acquiring, by the 3D camera, 3D image data of the head of the patient and transferring the acquired 3D image data to the computer;

processing, by the computer, the 3D image data to construct a head model of the patient;

constructing, by the computer, a spatial coordinate system based on the 3D camera, and calculating, by using the 3D image data, three-dimensional coordinates of feature points of the head of the patient in the spatial coordinate system; matching the head model of the patient with the head of the patient in the spatial coordinate system, and determining three-dimensional coordinates of a stimulation target on the head of the patient in the spatial coordinate system; and controlling, according to a spatial position of the stimulation target on the head of the patient, the articulated robot to move the TMS coil to the position of the stimulation target on the head of the patient to carry out magnetic stimulation treatment on the head of the patient.

6. The transcranial magnetic stimulation diagnostic and treatment device according to claim 1, wherein, a heat dissipating window is provided on a side surface of the base and is configured to dissipate heat of the controller.

7. A diagnostic and treatment method based on the transcranial magnetic stimulation diagnostic and treatment device according to claim 6, comprising the following steps:

making the patient lie on the horizontal translation platform, resting the head of the patient on the head rest, and controlling and adjusting, by the computer, a longitudinal position of the horizontal translation platform to position the head of the patient within an image acquisition range of the 3D camera;

acquiring, by the 3D camera, 3D image data of the head of the patient and transferring the acquired 3D image data to the computer;

processing, by the computer, the 3D image data to construct a head model of the patient;

constructing, by the computer, a spatial coordinate system based on the 3D camera, and calculating, by using the 3D image data, three-dimensional coordinates of feature points of the head of the patient in the spatial coordinate system; matching the head model of the patient with the head of the patient in the spatial coordinate system, and determining three-dimensional coordinates of a stimulation target on the head of the patient in the spatial coordinate system; and controlling, according to a spatial position of the stimulation target on the head of the patient, the articulated robot to move the TMS coil to the position of the stimulation target on the head of the patient to carry out magnetic stimulation treatment on the head of the patient.

8. The transcranial magnetic stimulation diagnostic and treatment device according to claim 1, wherein, a plurality of gimbal locking wheels are provided on the bottom of the base.

9. A diagnostic and treatment method based on the transcranial magnetic stimulation diagnostic and treatment device according to claim 1, comprising the following steps:

making the patient lie on the horizontal translation platform, resting the head of the patient on the head rest, and controlling and adjusting, by the computer, a longitudinal position of the horizontal translation platform to position the head of the patient within an image acquisition range of the 3D camera;

acquiring, by the 3D camera, 3D image data of the head of the patient and transferring the acquired 3D image data to the computer;

processing, by the computer, the 3D image data to construct a head model of the patient;

constructing, by the computer, a spatial coordinate system based on the 3D camera, and calculating, by using the 3D image data, three-dimensional coordinates of feature points of the head of the patient in the spatial coordinate system; matching the head model of the patient with the head of the patient in the spatial coordinate system, and determining three-dimensional coordinates of a stimulation target on the head of the patient in the spatial coordinate system; and controlling, according to a spatial position of the stimulation target on the head of the patient, the articulated robot to move the TMS coil to the position of the stimulation target on the head of the patient to carry out magnetic stimulation treatment on the head of the patient.

10. The diagnostic and treatment method according to claim 9, wherein, in the controlling step, in process of carrying out the magnetic stimulation treatment on the head of the patient, three-dimensional attitude information of the head of the patient is acquired by the 3D camera in real time, a latest spatial position of the stimulation target on the head of the patient is determined according to the three-dimensional attitude information acquired in real time, and finally, according to the latest spatial position of the stimulation target on the head of the patient, the articulated robot is controlled to move the TMS coil to the latest position of the stimulation target on the head of the patient to carry out precise magnetic stimulation treatment on the head of the patient in real time.

\* \* \* \* \*